(12) United States Patent
McMahon

(10) Patent No.: US 7,004,017 B1
(45) Date of Patent: Feb. 28, 2006

(54) MATERIALS TESTER LATCHING COUPLING DEVICE

(75) Inventor: Stephen Michael McMahon, Quincy, MA (US)

(73) Assignee: Instron Corporation, Canton, MA (US)

( * ) Notice: Subject to any disclaimer, the term of this patent is extended or adjusted under 35 U.S.C. 154(b) by 0 days.

(21) Appl. No.: 10/823,013

(22) Filed: Apr. 12, 2004

(51) Int. Cl.
*G01N 3/52* (2006.01)

(52) U.S. Cl. .......................................... 73/85
(58) Field of Classification Search ................ 277/314, 277/602, 616, 618, 619; 285/31, 33; 73/81–83, 73/85, 12.09, 12.12–12.14, 54.36, 818, 821, 73/825
See application file for complete search history.

(56) References Cited

U.S. PATENT DOCUMENTS

| | | | | |
|---|---|---|---|---|
| 1,538,007 A | * | 5/1925 | Schellin ...................... 277/616 |
| 3,445,120 A | * | 5/1969 | Barr ............................ 277/625 |
| 3,732,725 A | * | 5/1973 | Allen et al. ..................... 73/81 |
| 4,006,626 A | * | 2/1977 | Ruzicka et al. ............ 73/12.02 |
| 4,598,581 A | * | 7/1986 | Brekke ...................... 73/117.3 |
| 5,313,825 A | * | 5/1994 | Webster et al. ................. 73/81 |
| 5,411,087 A | * | 5/1995 | Taylor ........................ 166/264 |
| 5,686,652 A | * | 11/1997 | Pfund ........................ 73/12.04 |
| 6,193,238 B1 | * | 2/2001 | Sporre ........................ 277/609 |

* cited by examiner

*Primary Examiner*—Robert Raevis
(74) *Attorney, Agent, or Firm*—Levisohn, Berger & Langsam, LLP

(57) ABSTRACT

A latching coupling device for material testers is provided. The coupling can be connected and disconnected without the use of tools and includes a housing and interfacer. A spring within the latching coupling device serves to center the interfacer while snapping the interfacer shoulder and end face into compressive contact. The invention is preferably used in conjunction with penetration hardness testers and includes a penetration interfacer with an angled surface.

6 Claims, 6 Drawing Sheets

MATERIALS TESTER LATCHING COUPLING DEVICE

BACKGROUND OF THE INVENTION

1. Field of the Invention

The present invention is generally directed to a material testing machine and more specifically to a latching coupling device for attachment with a material testing system.

2. Description of Related Art

Material testing systems are used in a variety of fields and generally include an interfacer. The interfacer is most commonly a penetrator as used with penetration hardness testers. Penetration hardness testers are well-known in the art, and generally include a diamond or ball tipped penetrator means to apply minor and major loads of predetermined magnitudes through the penetrator to a test specimen in successive load cycles. The hardness is related to the depth of penetration of the penetrator into the surface when a selectable value of compressive force is applied to the penetrator. The testers generate results such as a Rockwell number or Brinell number. Other interfacers commonly used with material testing systems include compression platens, probes, grips, and the like.

Over the years, many material testing systems have been developed. In regards to penetration hardness testers, these systems use a variety of different mechanisms to attach and secure the penetrators to the penetration hardness testers. For example, as shown in FIG. 7, United Calibration Corp., of Huntington Beach, Calif., manufactures machines having a split collet arrangement that accept the ¼" shank of the diamond penetrator. The penetrator is gripped when the screw is tightened on the provided split collet clamp. The clamp must be tightened while the penetrator is in contact with a specimen under the maximum test load (this is sometimes referred to as "preloading the load string"). Also, the high test loads are borne by the contact between the penetrator shoulder and the end face. Because perfect perpendicularity of the penetrator shank and its shoulder, and the housing bore and its face, is realistically impossible, all four surfaces never have simultaneous contact. This assembly is overconstrained and the parts of the assembly may shift during use which results in inaccurate testing. Settling of the coupling during testing can affect the hardness measurement since penetration hardness testers measure the depth of penetration while applying a penetration load. Furthermore, this assembly is inconvenient because it requires a tool to tighten or loosen the clamping screw, at a specific torque, every time a different penetrator is used to test different materials at various loads. It is not uncommon for the coupling to be changed many times in one day and this routine becomes impractical and leads to unreliable test results.

Other testers, such as those manufactured by Newage Testing Instruments, Southampton, Pa., use a threaded penetrator that screws into the holder until the penetrator shoulder bottoms out. Similar to the United machines, the screw threads must be machined perpendicular to the seating shoulder. Commonly, the penetrators loosen due to everyday wear or because of poor installation. Users of the machine have no clear way of recognizing an alignment problem since the machine provides no clear indication of a loose penetrator. Once the penetrator becomes loose, data is greatly affected. Others, such as Wilson-Wolpert, use magnets in the housing to bring the penetrator into constant, compressive contact with the housing. Yet, this design is flawed because the magnet can attract and retain iron particles from the penetrator or working environment in general. Accordingly, contamination between the mating faces of the penetrator and the housing will affect data.

Another tester, known as the Instron/Wilson tester, made by the assignee of the present invention, uses a spring-loaded-ball assembly threaded into the housing to gently bear on a flat area on the side of the penetrator shank to hold the penetrator in place. This is an improvement over the previously described split collet and threaded designs for a number of reasons. Foremost, the use of a spring provides less overconstraint of the surfaces. Furthermore, with a spring-loaded-ball assembly, there is no need to preload the load string while mounting a penetrator. This type of tester also allows the penetrator to be changed without the use of tools. On the other hand, the spring-loaded-ball assembly of the Instron/Wilson tester can still overconstrain the assembly and lead to non-repeatability. With daily wear and changing the penetrator, the shank and bore can become displaced and non-perpendicular with continued use. Moreover, the spring-loaded-ball assembly is incapable of securing heavier penetrators in place.

Accordingly, what is needed is a latching coupling device that overcomes the problems associated with a typical materials testing assembly. The system should be easily implemented within the existing environment and should be adaptable and compatible with existing technology.

SUMMARY OF THE INVENTION

In accordance with the present invention, a latching coupling device for material testers is provided. This new device with the described features, preferably used in conjunction with penetration hardness testers, enables an improved manner of testing materials.

It is an object of the invention to provide a latching coupling device to be used in conjunction with material testing systems which substantially eliminates the inaccuracies of prior material testing systems.

Another object of the invention is to provide such an improved apparatus which is easy to operate, is substantially unchanging over time, and produces reliable and accurate results.

Yet another object of this invention is to provide such a device which advantageously employs current technology to provide improved results and may be readily adapted to provide test data for a variety of material testing systems.

It is a further object of the invention to provide an improved method of conducting materials testing which produces reliable and accurate results.

Yet another object of the invention is to provide a latching coupling that can be assembled and disassembled without the use of tools.

It is another object of the invention to provide a latching coupling for material testers which can accommodate both inventive penetrators and conventional penetrators.

Other objects, advantages, and features of this invention will become apparent from the following description.

The inventive latching coupling device is for use with material testers and has an interfacer with a shank and shoulder; a housing with a bore, a resilient member such as a spring or an elastomer O-ring, and a groove. The groove is formed within the bore, and the resilient member is disposed in the groove. The housing can be connected to the interfacer so that they lock together. The latching coupling device can minimize contact between the housing and interfacer so that only the shoulder and end face have contact. That is, the shank of the interfacer and the inner wall of the bore of the housing substantially do not contact each other except at the resilient member. The interfacer can be adapted for use with a spring-loaded assembly and can also be a penetrator to be used with penetration hardness testers. In another embodiment, the resilient member is located within a groove in the interfacer, which results in an "inside-out" configuration.

Methods of securing an interfacer to a materials testing machine are also provided.

DETAILED DESCRIPTION OF THE DRAWINGS AND THE PREFERRED EMBODIMENTS

The present invention relates to a latching coupling device to be used in conjunction with a material testing system. Various modifications to the preferred embodiment will be readily apparent to those skilled in the art and the general principles herein may be applied to other embodiments. The present invention is not intended to be limited to the embodiment shown but is to be accorded the widest scope consistent with the principles and features described herein. Preferably, the present invention is to be used with the material testing system described by Merck, Jr. et al. in U.S. Pat. No. 6,142,010, the teachings of which are incorporated by reference herein.

Description will now be given of the inventive latching coupling device with reference to FIGS. 1–6. It should be noted that these drawings are exemplary in nature and in no way serve to limit the scope of the invention. The latching coupling device comprises three main parts: an interfacer, housing, and spring. Preferably, the interfacer is a penetrator as used commonly in the field of materials testing systems.

Figure 1:
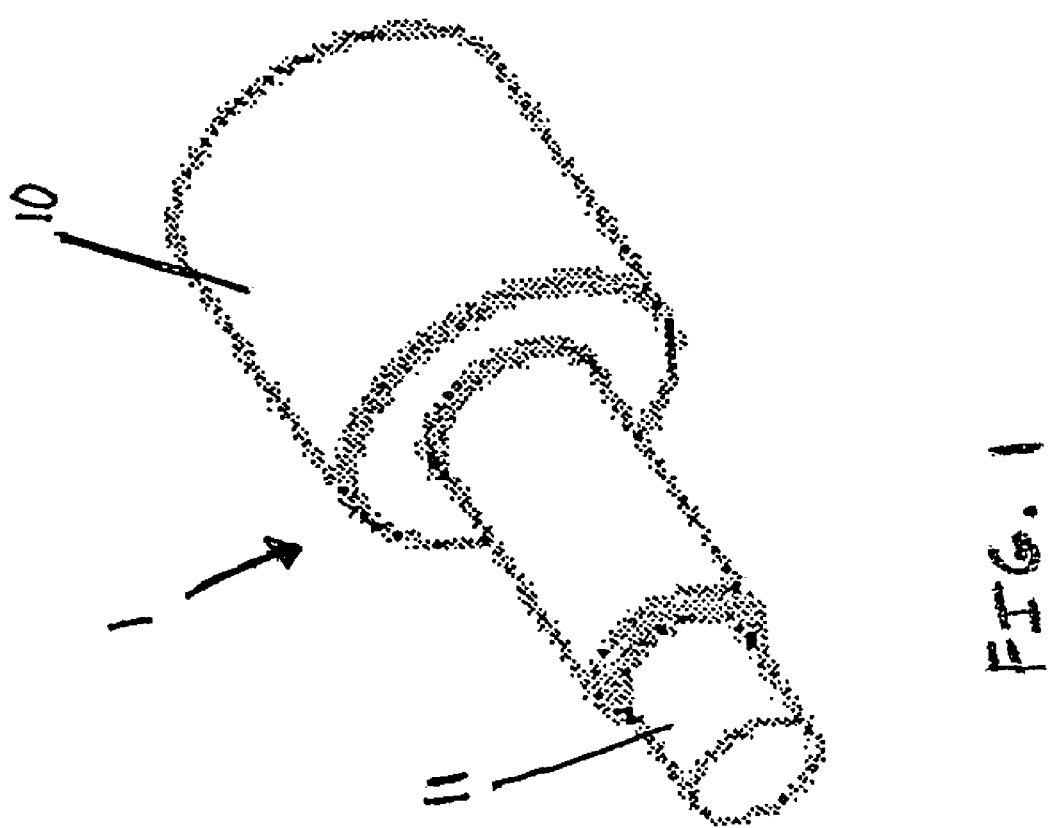
FIG. 1 is a perspective view of the latching coupling device in assembled form.
Figure 2:
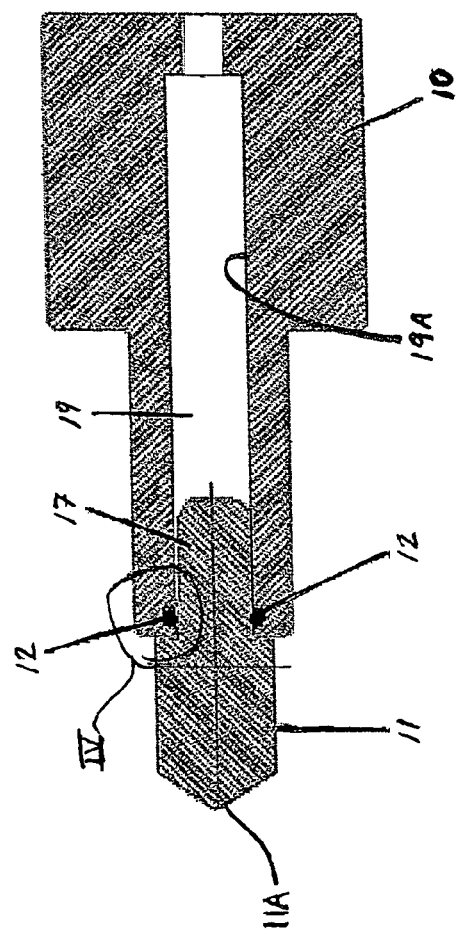
FIG. 2 is a cross-sectional view of the latching coupling device in assembled form.
Figure 3:
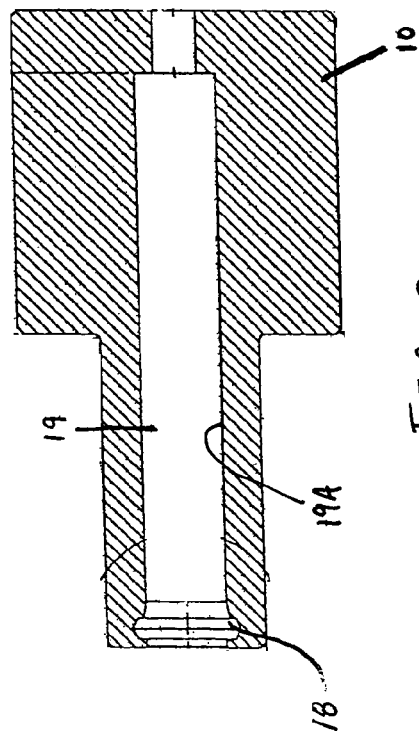
FIG. 3 is a cross-sectional view of the housing.
Figure 4:
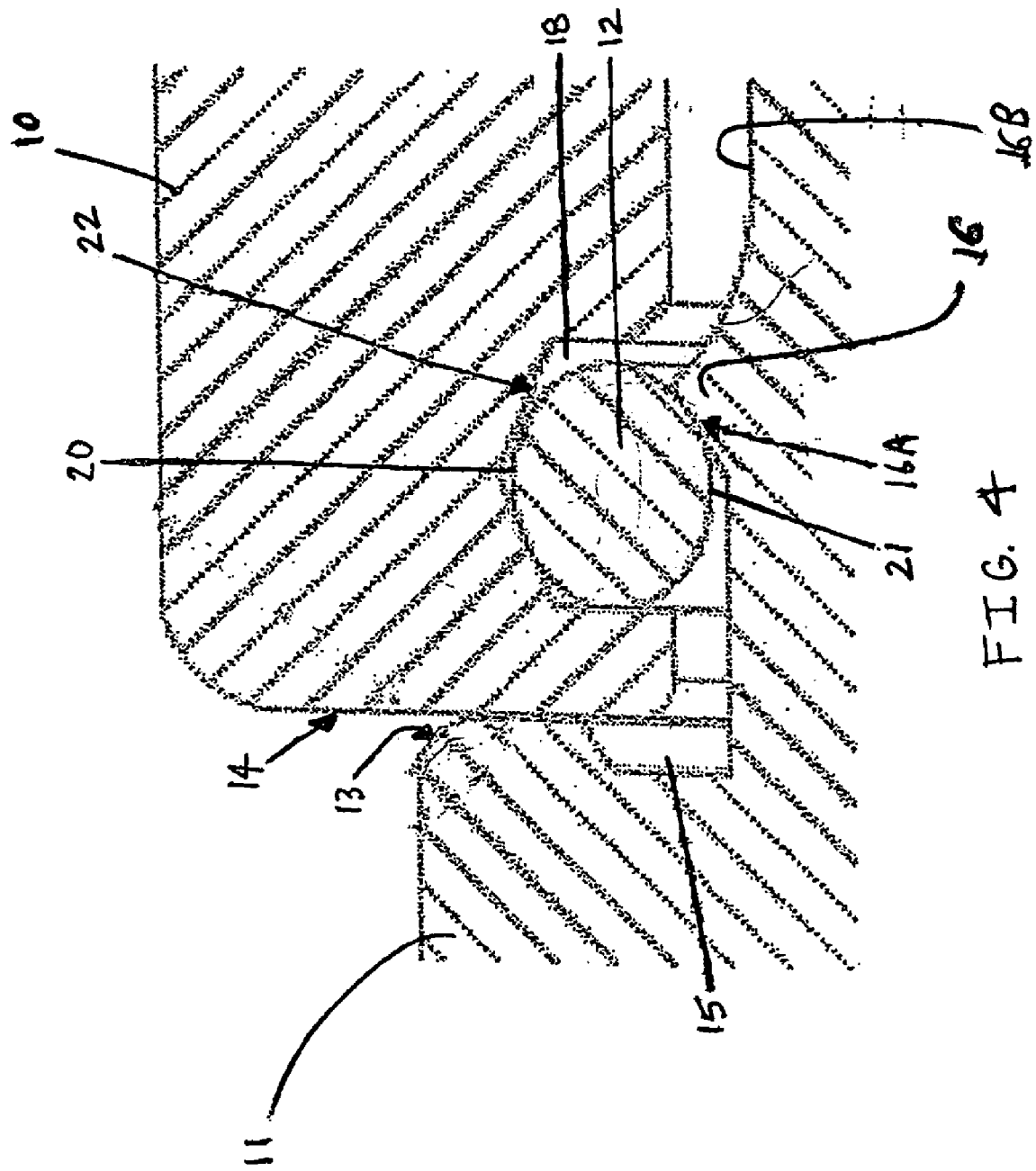
FIG. 4 is an enlarged cross-sectional view of area IV of FIG. 2.

FIG. 1 shows the housing 10 and interfacer 11 of the latching coupling device. As shown in FIGS. 2–4, the latching coupling device 1 of the present invention comprises a housing 10, an interfacer 11, and a resilient member shown as spring 12.

Housing 10 has a bore 19 with inner bore walls 19A and groove 18. Housing 10 is designed to receive interfacer 11. Interfacer 11 has a working end 11A, a shank 17 with an annular flange 16 having an angled surface 16A, and a trepanned relief 15 (see FIG. 4).

Figure 5A:
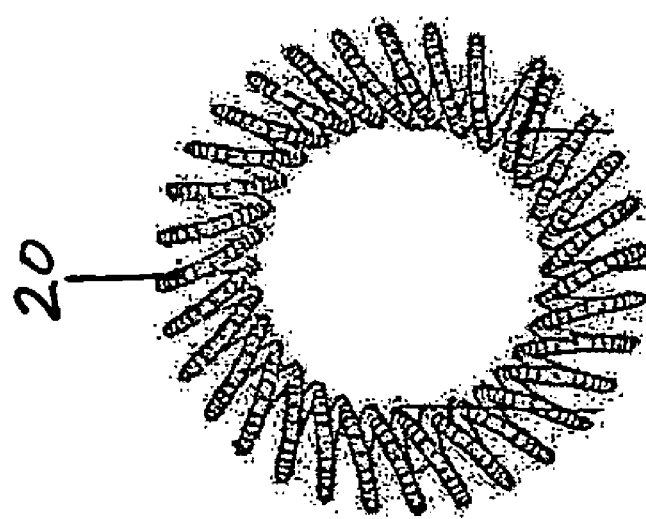
FIG. 5A is a top view of a spring for use in the invention.
Figure 5B:
FIG. 5B is a side view of the spring of FIG. 5A.

As shown in FIG. 5A, the spring 12 has a top portion 20 and a bottom portion 21. As shown in FIG. 5A and FIG. 5B, the spring 12 is preferably a canted coil spring (alternatively, the spring could be an elastomer O-ring) which maintains nearly constant force over a wide range of working deflections. The preferred spring is manufactured by Bal Seal Engineering. This type of spring allows the spring to compensate for large tolerances between mating surfaces and wide temperature variables without any significant change from its initial force. As shown in FIG. 4, the spring 12 is installed into the groove 18 of the housing 10. The groove 18 has a groove wall 22.

Interfacer 11 has a shank 17 which is insertable into bore 19 of housing 10. Latching of the coupling device 1 is accomplished by connecting housing 10 to interfacer 11. The coils of spring 12 allow the interfacer 11 to be inserted into housing 10 so that the coils of spring 12 grip the interfacer shank 17 with a full 360-degree radial force.

When the interfacer 11 is fully inserted into housing 10, spring 12 bears against the interfacer angled surface 16A which gives rise to a longitudinal force so that the interfacer shoulder 13 snaps against the end face 14. The user hears an audible click which indicates the latching of the coupling device. The interfacer angled surface 16A is in contact with the coils of spring 12 over 360-degrees which allows complete circumferential contact between interfacer shoulder 13 and end face 14. Additionally, because spring 12 provides a 360-degree radial grip on the interfacer shank 17, the spring 12 centers the interfacer shank 17 within the bore 19 such that there is no contact between interfacer shank 17 and the inner bore walls 19A. This positioning only allows contact between interfacer shoulder 13 and end face 14. The interfacer shoulder 13 has a trepanned relief 15 which eliminates any potential unwanted contact between housing 10 and interfacer 11 and leaves an annular ring of contact between shoulder 13 and end face 14.

An important aspect of the present invention is the ability to utilize the latching coupling device 1 with previous spring-loaded-ball assemblies, particularly those manufactured by Instron, the instant assignee. The interfacer shank 17 of interfacer 11 has a flat section 16B so that the present invention can be used in conjunction with Instron spring-loaded-ball assemblies. This adaptability enhances the overall value and versatility of the latching coupling device 1. Additionally, this invention allows the latching coupling device 1 to sustain heavier penetrator assemblies without the use of a setscrew due to the compressive preload which is generated by having the spring 12 bear against the interfacer angled surface 16. The present invention can be used with a number of different material testing systems. Furthermore, the interfacer can be manufactured in a variety of ways and from various materials. For example, the interfacer may be steel, diamond tipped, or of carbide or steel balls.

Figure 6:
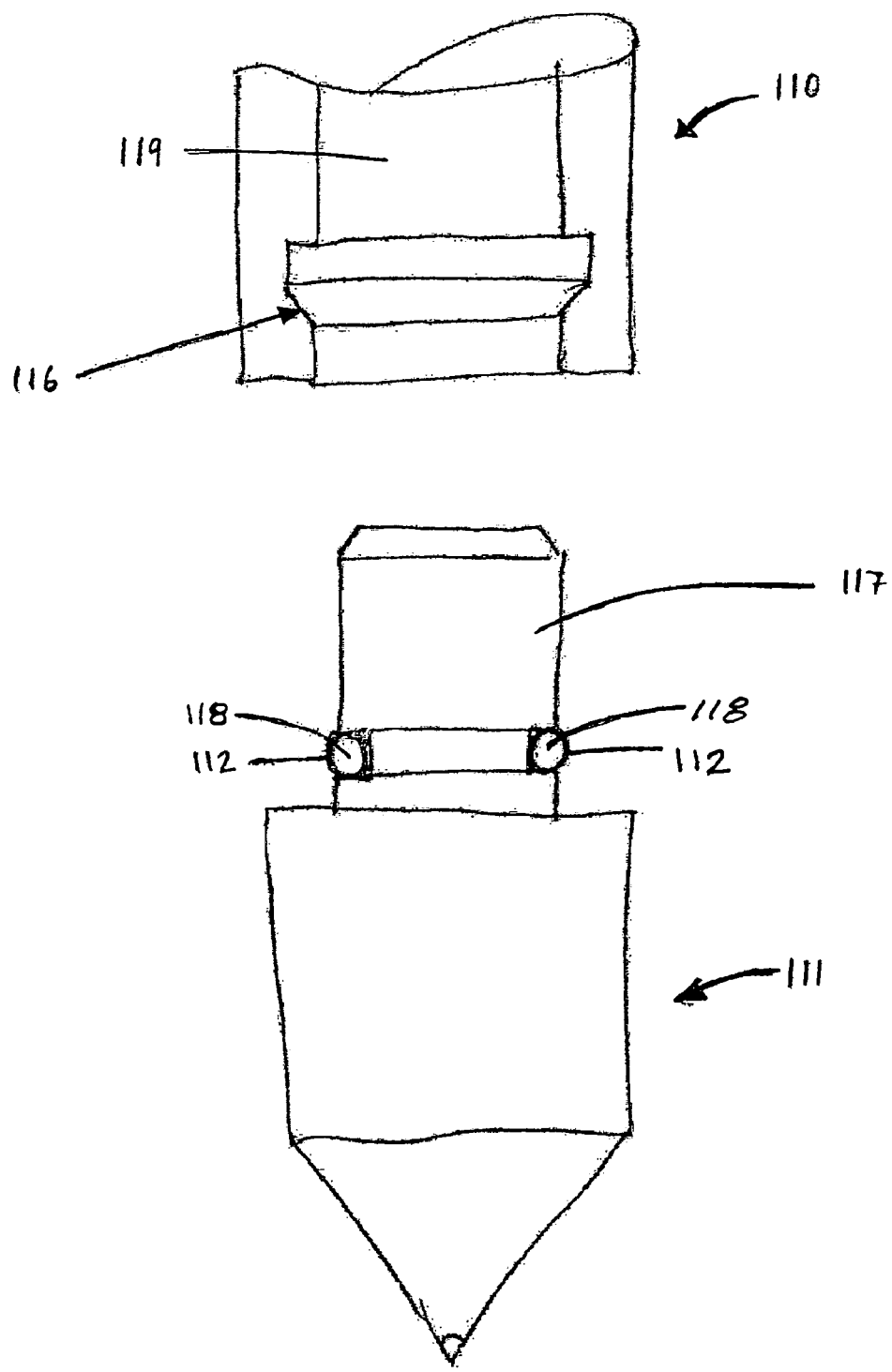
FIG. 6 is a side view of another embodiment of the present invention.
Figure 7:
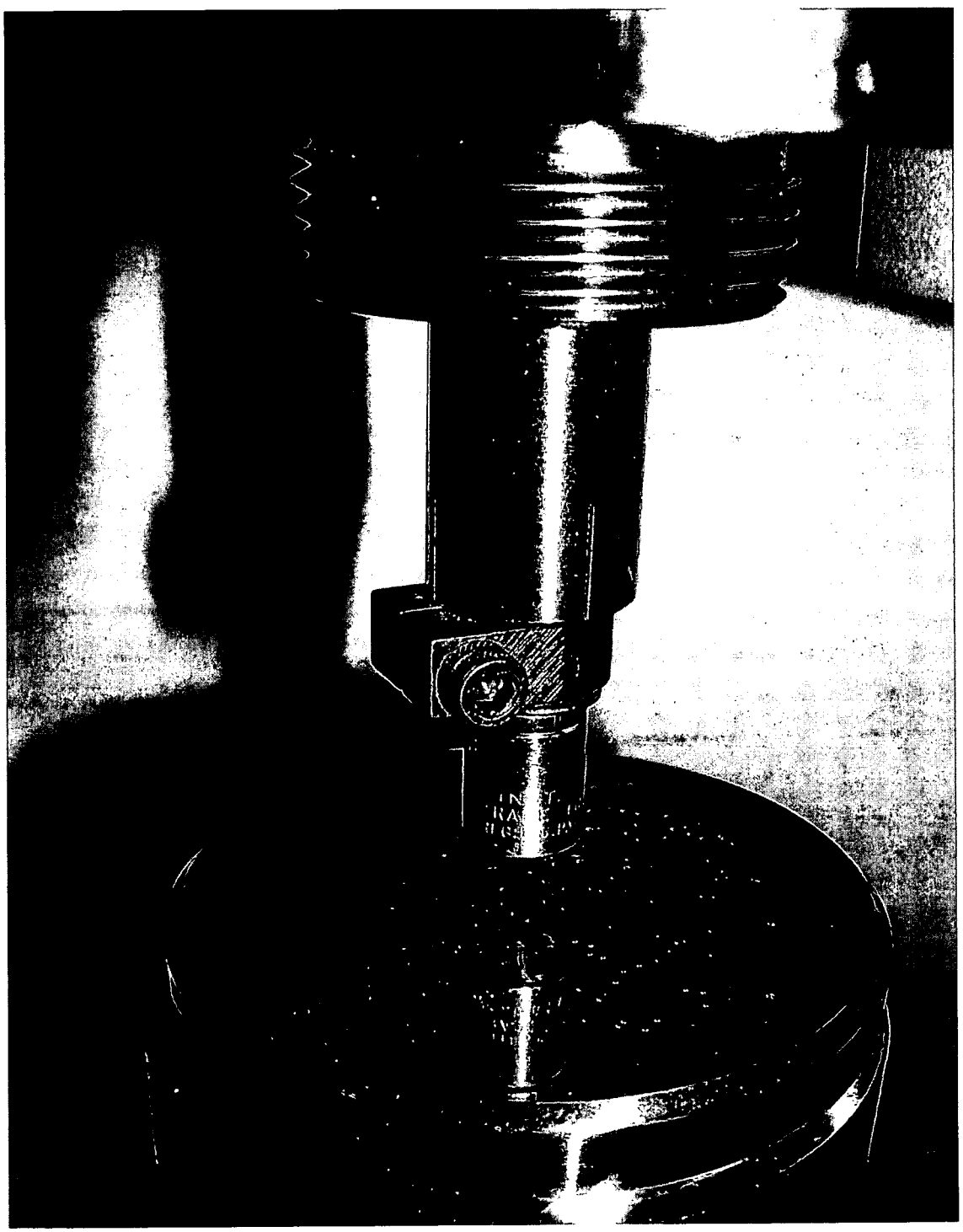
FIG. 7 is a perspective view of a conventional coupling device.

Another embodiment of the present invention is shown in FIG. 6. The spring 112 (again, an elastomer O-ring could be used instead) is installed in a groove 118 in the interfacer shank 117 of interfacer 111 and the angled surface 116 is machined in bore 119 of housing 110. With this embodiment, the spring 112 is dragged along the housing bore 119. Thus, housing 110 may be manufactured to either minimize wear of its bore 119 or to minimize wear of the spring 112. Since each interfacer 111 has its own, the life of any resilient member is dependent on how many times that interfacer is installed and removed and not the total of how many times the housing 10 receives an interfacer, as is the case with the previously described first embodiment.

This invention is not limited to the above described preferred embodiments; other embodiments are considered to be within the scope of this invention as defined by the appended claims.

What is claimed is:

1. A materials tester latching coupling device comprising:
   a housing securable to a material tester, having a bore, a groove within said bore, and a groove wall;

an interfacer having a shank, a shoulder, and an annular flange formed on said shank, said shank insertable into said bore, said interfacer comprising a penetrator; and a resilient member positioned within said groove and having first and second portions, wherein when said shank is inserted into said bore, said first portion of said resilient member is supported by said annular flange of said interfacer and said second portion of said resilient member is supported by said groove wall of said housing, and wherein said latching coupling device is used in conjunction with a penetration hardness tester.

2. A materials tester latching coupling device as claimed in claim 1, wherein said annular flange has an angled surface.

3. A materials tester latching coupling device as claimed in claim 1, wherein when said shank is inserted into said bore, said shank and an inner wall of said bore substantially do not contact each other except at said resilient member.

4. A materials tester latching coupling device as claimed in claim 1, wherein said shank includes a flat portion adapted for use with a spring-loaded-ball assembly.

5. A materials tester latching coupling device as claimed in claim 1, wherein said resilient member comprises one of a spring and an elastomer O-ring.

6. A materials tester latching coupling device as claimed in claim 1, wherein said resilient member is a canted coil spring.

* * * * *